(12) United States Patent
Nakanishi

(10) Patent No.: US 7,001,971 B2
(45) Date of Patent: Feb. 21, 2006

(54) POLYHYDRIC ALCOHOL-MODIFIED SILICONE AND COSMETIC MATERIAL CONTAINING SAME

(75) Inventor: Tetsuo Nakanishi, Gunma-Ken (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 47 days.

(21) Appl. No.: 10/388,229

(22) Filed: Mar. 14, 2003

(65) Prior Publication Data

US 2004/0146472 A1   Jul. 29, 2004

Related U.S. Application Data

(63) Continuation-in-part of application No. 10/005,672, filed on Dec. 7, 2001, now abandoned.

(30) Foreign Application Priority Data

Dec. 8, 2001   (JP) .............................. 2000-374342

(51) Int. Cl.
*C08K 77/50* (2006.01)

(52) U.S. Cl. ............................ 528/29; 528/31; 528/35; 556/434; 424/65; 424/70.12

(58) Field of Classification Search ................ 528/29, 528/35, 31; 556/434; 424/65, 70.12
See application file for complete search history.

(56) References Cited

U.S. PATENT DOCUMENTS

| 4,431,789 A | * | 2/1984 | Okazaki et al. ............... 528/15 |
| 5,306,838 A | | 4/1994 | Shioya et al. |
| 5,916,992 A | * | 6/1999 | Wilt et al. ................... 528/15 |
| 5,969,172 A | | 10/1999 | Nye |
| 6,001,140 A | * | 12/1999 | Grabowski et al. ........... 44/320 |
| 6,150,311 A | | 11/2000 | Decoster et al. |
| 6,268,519 B1 | * | 7/2001 | Nye ........................... 556/445 |
| 6,660,281 B1 | * | 12/2003 | Nakanishi et al. ........... 424/401 |
| 6,790,451 B1 | * | 9/2004 | Nakanishi .................. 424/401 |

FOREIGN PATENT DOCUMENTS

EP   0953333 A1   11/1999

* cited by examiner

*Primary Examiner*—Margaret G. Moore
(74) *Attorney, Agent, or Firm*—Millen, White, Zelano, Branigan, P.C.

(57) ABSTRACT

The present invention generally relates to a polyhydric alcohol-modified silicone having the formula (I):

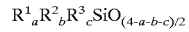

wherein the variables are defined herein.

20 Claims, No Drawings

POLYHYDRIC ALCOHOL-MODIFIED SILICONE AND COSMETIC MATERIAL CONTAINING SAME

CROSS-REFERENCE TO RELATED APPLICATION

This application is a continuation-in-part of application Ser. No. 10/005,672, filed Dec. 7, 2001, now abandoned.

This invention relates to a novel polyhydric alcohol-modified silicone, and to cosmetic materials containing this substance. When it is used as an oil base, cosmetic materials containing the polyhydric alcohol-modified silicone have excellent adhesion to the skin, are not sticky and have a clean feel, and when it is used as an emulsifier, they have excellent emulsification stability.

In general, human secretions such as sweat, tears and sebum cause makeup to disintegrate. In particular, sebum secreted from the skin adds to the effect of the oil base of cosmetic materials, and the excessive wetting of powders in the cosmetic materials is a major factor in their disintegration. Hence, to reduce oils in cosmetic materials which remain on the skin, volatile oils such as octamethylcyclotetrasiloxane and decamethylcyclopentylsiloxane are sometimes blended with the oil bases used.

External factors such as friction and water, etc., adversely affect how long makeup stays on the skin. Thus, to improve the ability of makeup to stay on the skin which is adversely affected by water-containing substances such as sweat and tears, silicone oil is blended with cosmetics to prevent the loss of water-soluble components in the skin or sebum, exert a protective effect on the skin and increase water repellence.

For example, a silicone oil such as dimethylpolysiloxane has such features as a light feel, outstanding water repellence and high safety, and has therefore been widely used as an oil in cosmetic materials in recent years.

Although polysiloxanes have excellent characteristics when used in oils for makeup, the skin is maladapted to them. They also lack a sufficient moisturizing effect and have a "squeaky" feel.

Water repellence was not much improved in foundations and makeup, while in skin care products such as milky lotions, an oil was needed with water repellence, light touch and good skin adaptability.

A silicone oil in which a fluoroalkyl group is introduced into dimethylpolysiloxane (Japanese Patent Laid-Open Hei 2-95912 (Koho)) has high oil repellence compared with dimethylpolysiloxane. However, if the fluoroalkyl group content is high, although sufficient oil repellence is obtained, the resulting oil has a heavy feel, and as it is insoluble in volatile oil bases such as octamethylcyclotetrasiloxane and decamethycyclopentasiloxane, it is not easy to use. Conversely, if the fluoroalkyl group content is low so that it dissolves in these volatile oil bases, sufficient oil repellence is not obtained, and it does not feel like it is adhering to the skin.

In recent years, although silicone oil is being used as an oil base in water-oil (W/O) emulsifions), water-oil emulsions containing this silicone oil are not very stable in emulsifiers such as the polyoxyalkylene fatty acid esters used conventionally.

Thus, a method of using polyoxyalkylene-modified organopolysiloxane (polyether-modified silicone), which is highly miscible with silicone oil, as a surfactant in the above-mentioned water-oil emulsions is disclosed in Japanese Patent Laid-Open Sho 61-293903, 61-293904, 62-187406, 62-215510, 62-216635 (Koho).

To obtain an emulsifion for cosmetics use, not only silicone oil but also ester oils and hydrocarbon oils are often used together as an oil base, but polyether-modified silicone had inferior emulsifying power in such a mixed oil base system, and it was difficult to obtain a stable water-oil emulsion.

To solve this problem, a method of using an organopolysiloxane having a long chain alkyl group and a polyoxyalkylene group represented by the following formula as an emulsifier, is proposed in Japanese Patent Laid-Open Sho 61-90732 (Koho).

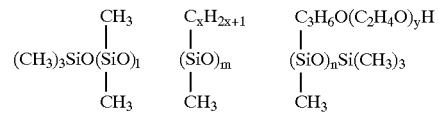

However, although the above-mentioned organopolysiloxane compound had excellent emulsifying power in a mixed oil base system with a large amount of ester oils and hydrocarbon oils, in a mixed oil base system with a large amount of silicone oil, it was difficult to obtain a stable emulsion which did not undergo time-dependent changes. Therefore, it was desired to obtain an emulsifier having excellent emulsifying performance in oil bases used for general cosmetic materials such as silicone oil, ester oils and hydrocarbon oils, and a suitable emulsifier for cosmetics use which was stable over time.

In skin cleansing agents, since cosmetic materials such as lipstick, foundation, eye shadow, eyeliner and mascara contain a large amount of solid oils, emulsions using cleansers do not easily dissolve and emulsify these oils, and therefore it is difficult to remove dirt completely. Hence, cleansing agents having an oily base as the main component were used. However, good cosmetic materials which do not easily fall off and last well have recently been developed, and in summer in particular when people sweat profusely, makeup materials have appeared on the market which are blended with oil bases such as annular silicones and polymers having high film-forming ability. Also, in cosmetic materials for the hair, to protect the hair, give it body, resilience and a good sheen, various substances are blended such as high polymer silicones and polymers having good film-forming ability.

Thus, although cleansing agents using nonionic surfactants and polyether-modified silicone had been used to remove cosmetic products which did not easily fall off or which had high hair protecting effect, it was desirable to develop a cleansing agent composition which had still greater cleansing power to remove cosmetic materials with enhanced functionality such as film-forming ability.

Various glycerol-modified silicones have been reported which improve the "squeaky" feel of silicone, have better skin compatibility and are more effective nonionic surfactants. For example, oil bases are mentioned in Japanese Patents Laid-Open Hei 6-157236 and 9-71504, and Japanese Patents Laid-Open Hei 10-310504-310509 with fluoroalkyl co-modification, surfactants are mentioned in Japanese Patent Publication Sho 62-34039, Japanese Patent 2613124 and Japanese Patent 2844453 which describe glycerol-modified silicone compounds, and cosmetics using these are mentioned in Japanese Patent Laid-Open Hei 8-22811, Japanese Patent 2587797 and Japanese Patent 2601735.

As polyhydric alcohol-modified silicone compounds which have a hydroxyl group, sugar and polysaccharide-modified silicone compounds have also been reported. A modified silicone compound which has a sugar residue is disclosed in Japanese Patent Laid-Open Hei 5-186596, and its application as an emulsifier is disclosed in Japanese Patent Laid-Open Hei 6-145023, 7-41414 and 7-41416.

In all these cases, by using a polyhydric alcohol-modified silicone such as glycerine, the "squeaky" feel of silicone is reduced and the stickiness of glycerine oil bases is suppressed by the addition of silicone.

It is therefore an object of this invention to provide a modified silicone compound which does not increase in viscosity when mixed with water as in the case of polyether-modified silicones, and has less feeling of stickiness. Other desirable features are rapid cleansing of oil residues, improvement of stickiness and better miscibility with silicone oil bases which were defects of prior art polyhydric alcohol-modified silicones, light feel with water repellence, user comfort and feeling of skin adhesion. It also aims to provide a modified silicone compound having excellent emulsifying power and emulsion stability with regard to oil bases such as the silicone oils used in cosmetic products, and cosmetic materials containing them.

The Inventor found, as a result of studies to achieve the above objects, that when the silicone compound obtained by the addition reaction of a polyhydric alcohol-substituted hydrocarbon group which has at least two hydroxyl groups and a silicone compound with an organohydrogen polysiloxane was used as an oil base or an emulsifier, it had extremely high affinity with silicone oil bases and excellent emulsifying power, and that the stability of the emulsion obtained was very good.

Moreover, the Inventor found that when the silicone compound obtained by the addition reaction of a polyhydric alcohol-substituted hydrocarbon group, a silicone group and an organic group having a long chain alkyl portion to an organohydrogen polysiloxane was used as an emulsifier, it had high affinity with oil bases used for general cosmetic materials such as silicone oils, ester oils and hydrocarbon oils and excellent emulsifying power, the stability of the emulsion obtained over time was good, and it was very effective when used in makeup.

Thus, in Japanese Patent Laid-Open Hei 7-197055, regarding silicone compounds in which silicone is further grafted onto the main silicone chain, it is recorded that a silicone compound obtained by grafting a silicone compound onto an organohydrogen polysiloxane by an addition reaction, has good low temperature characteristics as a silicone oil, but no mention is made of its use in cosmetic materials. The Inventor also found that it is effective in cosmetic materials by modifying it with a polyhydric alcohol-substituted hydrocarbon group.

Further, the Inventor found that by using the above-mentioned silicone compound in the low molecular weight range, skin cleansing compositions are obtained which have an excellent cleansing effect not only on skin dirt but also on makeup which does not come off easily, and which have a very good feel during and after washing.

This invention is a polyhydric alcohol-modified silicone having the following general formula (1):

(where, $R^1$ is, identical or different, selected from the group consisting of an alkyl group, aryl group, aralkyl group, fluorine-substituted alkyl group, amino-substituted alkyl group and carboxyl-substituted alkyl group, which have 1–30 carbon atoms, and organic groups represented by the following general formula (2):

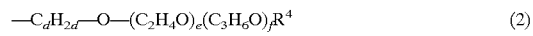

(where, $R^4$ is a hydrocarbon group having 4–30 carbon atoms, or $R^5$—(CO)— (where $R^5$ is a hydrocarbon group having 1–30 carbon atoms), d, e and f are integers in the range 0.d.15, 0.e.50 and 0.f.50, respectively);

$R^2$ is represented by the following general formula (3):

(where, Q is a bivalent hydrocarbon group having 3–20 carbon atoms which may contain at least an ether linkage or ester bond, and X is a polyhydric alcohol-substituted hydrocarbon group which has at least two hydroxyl groups);

$R^3$ is an organosiloxane having the following general formula (4):

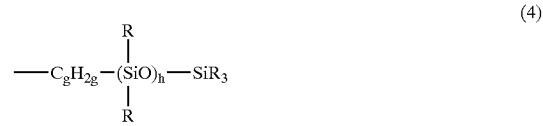

(where, R groups each represent a 1–30C alkyl group, an aryl group, an aralkyl group or a fluorinated alkyl group, g and h are integers in the range 1.g.5 and 0.h.500, respectively), and a, b and c are in the range 1.0.a.2.5, 0.001.b.1.5 and 0.001.c. 1.5, respectively).

Hereafter, this invention will be described in detail.

The silicone branch type polyhydric alcohol-modified silicone compound a) used in this invention is represented by the following general formula (1):

$R^1$ may be an alkyl group such as methyl, ethyl, propyl, butyl, pentyl, hexyl, heptyl, octyl, nonyl and decyl; a cycloalkyl group such as cyclopentyl and cyclohexyl; an aralkyl group such as phenyl, tolyl, benzyl and phenethyl; or a fluorosubstituted alkyl group such as trifluoropropyl and heptadecafluorodecyl. Other examples are amino-substituted alkyl groups such as 3-amino propyl and 3-[(2-amino ethyl)amino]propyl, and carboxy-substituted alkyl groups such as 3-carboxypropyl.

A part of $R^1$ may be the organic group represented by the general formula —$C_dH_{2d}$—O—$(C_2H_4O)_e(C_3H_6O)_fR^4$. Here, $R^4$ is an organic group represented by a hydrocarbon group having 4–30 carbon atoms or $R^5$—(CO)—, where $R^5$ is a hydrocarbon group having 1–30 carbon atoms.

d, e and f are integers in the range 0.d.15, 0.e.50 and 0.f. 50, respectively. A part of this $R^1$ is an alcoholic residue or an alkenyl ether addition product residue, whereof a specific example is:

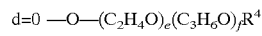

In this case, if e=0 and f=0, it is an alkoxy group having 4–30 carbon atoms, for example lower alkoxy groups such as butoxy to higher alkoxy groups such as oleoxy or stearoxy, i.e., cetyl alcohol, oleyl alcohol and stearyl alcohol, or fatty acid residues such as acetic acid, lactic acid, butyric acid, oleic acid, stearic acid and behenic acid.

If e and f>1, it is an alcoholic residue of an alkylene oxide addition product (the terminal is a hydroxyl group) of a higher alcohol.

Here, when d is 1 or more, e=0, and f=0, it is particularly desirable that d is 3, 5 or 11. In this case, it is an allyl ether, pentenyl ether or undecenyl ether residue, or an allyl stearyl ether residue, pentenyl behenyl ether residue, or undecenyl oleyl ether residue depending on the substituent group $R^4$. When e or f is not 0, an alkoxy group and an ester group are present via a polyoxyalkylene.

Here, whatever e and f may be, when d is 0, the compound has less resistance to hydrolysis, and if d is 15 or higher, it has a strong oily smell, therefore it is preferable that it is in the range of 3–5.

It is preferable that 50% or more of $R^1$ is methyl, but it is more preferable that it is 70% or more, and it may also be 100%.

$R^2$ is represented by the following general formula (3).

$$-Q\text{-}O\text{---}X \quad (3)$$

Here, Q represents a bivalent hydrocarbon group having 3–20 carbon atoms which may contain an ether linkage or an ester bond. Examples are —$(CH_2)_2$—, —$(CH_2)_3$—, —$CH_2CH(CH_3)CH_2$—$(CH_2)_4$—, —$(CH_2)_5$—, —$(CH_2)_6$—, —$(CH_2)_7$—$(CH_2)_8$—, —$(CH_2)_2$—$CH(CH_2CH_2CH_3)$—, —$CH_2$—$CH(CH_2CH_3)$—, —$(CH_2)_3$—O—$(CH_2)_2$—, —$(CH_2)_3$—O—$CH_2CH(CH_3)$—, —$(CH_2)_2$—O—$(CH_2)_2$—, —$(CH_2)_3$—O—$CH_2CH(CH_3)$—, and —$CH_2$—$CH(CH_3)$—$COO(CH_2)_2$—.

X is a polyhydric alcohol-substituted hydrocarbon group which has at least two hydroxyl groups, and is preferably a hydrocarbon group chosen from glycerine and a sugar derivative.

The glycerol may be the compound having the formula shown below. Q in the following formula is the same as Q in formula (3), and s and t in the formula are integers in the range 1–20, and u is an integer of 1 or 2. Also, some hydroxyl groups in the following compound may be replaced by alkoxy groups or ester groups.

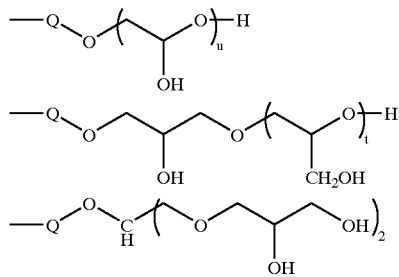

The sugar residue derived from a monosaccharide, oligosaccharide or polysaccharide may be a monosaccharide group such as glycosyl, mannosyl, galactosyl, ribosyl, arabinosyl, xylosyl or fructosyl, an oligosaccharide group such as maltosyl, cellobiosyl, lactosyl or maltotriosyl, or a polysaccharide group such as cellulose or starch, but monosaccharides and oligosaccharides are preferred.

$R^3$ is the silicone compound represented by the following general formula (4).

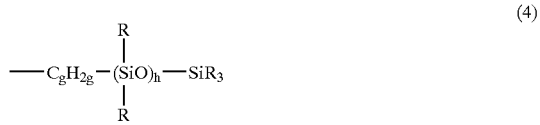

Here, R groups each represent a 1–30C alkyl group, an aryl group, an aralkyl group or a fluorinated alkyl group, g in the formula is an integer in the range 1–5, and when the compound is synthesized from a reaction between a vinylsiloxy group and a SiH group, g is 2. h is 0–500, but preferably 1–50. When h is larger than 500, problems such as poor reactivity with the main chain may arise.

In one preferred embodiment, $R^1$ in the formula (1) can be the same as R in formula (4) and Formula (iii). In another preferred embodiment, it is preferable that 50% or more, more preferably 70% or more, or alternatively 100% of $R^1$ and/or R are methyl.

Regarding the silicone compound in the above (4), a silicone compound with improved asymmetrical blockage rate may be synthesized using the well-known method by synthesizing an asymmetrical vinylsiloxane by an equilibration reaction between divinyltetramethyldisiloxane, hexamethyldisiloxane and octamethylcyclotetrasiloxane, and performing a ring opening polymerization of hexamethylcyclotrisiloxane by a 5 coordination silicon complex catalyst or an anion polymerization catalyst.

The silicone compound of the above-mentioned formula (1) used in this invention may be easily synthesized by carrying out an addition reaction of an organohydrogen polysiloxane, an allyl compound ether compound represented by the following (i) and (ii), a vinylsilicone compound represented by the following (iii), and if necessary an alkylene compound such as hexane, in the presence of a platinum catalyst or a rhodium catalyst.

$$C_3H_5\text{—}O\text{—}(C_2H_4O)_e(C_3H_6O)_f\text{-}R^4 \quad (i)$$

$$C_3H_5\text{—}O\text{—}X \quad (ii)$$

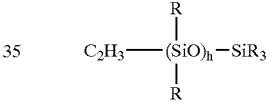 (iii)

(R, $R^4$, X, e, f, and h are the same as those in the above formulae.)

Here, the organohydrogenpolysiloxane may be straight chain or cyclic, but it is usually preferably straight chain so that the addition reaction proceeds smoothly.

The mixing proportion of the sum total of the organohydrogen polysiloxane, the polyhydric alcohol compound represented by the above general formula (ii), the silicone compound represented by the above general formula (iii), the alkylene compound and/or the organic compound represented by the above general formula (i), is 0.5–2.0 and preferably 0.8–1.2 in terms of the mole ratio of SiH groups and terminal unsaturated groups.

The above addition reaction is preferably carried out in the presence of a platinum catalyst or a rhodium catalyst. Specific catalysts which may be used are chloroplatinic acid, alcohol-modified chloroplatinic acid and chloroplatinic acid-vinyl siloxane complex.

The amount of catalyst used may be the usual amount as a catalyst, but it is preferably 50 ppm or less, or more preferably 20 ppm or less, in terms of the amount of platinum or rhodium. The above addition reaction may be performed in an organic solvent if necessary. The organic solvent may be an aliphatic alcohol such as methanol, ethanol, 2-propanol and butanol, an aromatic hydrocarbon such as toluene and xylene, an aliphatic or alicyclic hydrocarbon such as n-pentane, n-hexane and cyclohexane, or a halogenated hydrocarbon such as dichloromethane, chloroform and carbon tetrachloride. There is no particular limitation on the reaction conditions, but it is preferable to perform the reaction under reflux for 1 to 10 hours.

a is 1.0–2.5, but preferably 1.2–2.3. When a is smaller than 1.0, miscibility with the oil base falls, and it is difficult to obtain a stable water-oil emulsion. When a is greater than 2.5, hydrophilic properties are poor, so it is also difficult to obtain a stable water-oil emulsion.

b is 0.001–1.5, but preferably 0.05–1.0. When b is smaller than 0.001, hydrophilic properties are poor, so it is difficult to obtain a stable water-oil emulsion. When it is larger than 1.5, hydrophilic properties are too marked, so it is also difficult to obtain a stable water-oil emulsion.

c is 0.001–1.5, but preferably 0.05–1.0. When c is smaller than 0.001, miscibility with the silicone oil falls, and it is difficult to obtain a stable water-oil emulsion. When it is larger than 1.5, hydrophilic properties are poor, so it is also difficult to obtain a stable water-oil emulsion.

From the viewpoint of the emulsion, there is no particular limitation on the weight average molecular weight of the silicone compound of formula (1), but 500–200000 and particularly 1000–100000 are to be preferred.

When used as a skin cleansing composition, it is desirable that the weight average molecular weight of the silicone compound of formula (1) is 4000 or less, but 2000 or less and particularly 1500 or less are to be preferred.

The cosmetic material of this invention contains a) the above-mentioned polyhydric alcohol-modified silicone as an indispensable component. It may further comprise at least one of a group comprising b) an oil base, c) a compound having an alcoholic hydroxyl group in its molecular structure, and d) water. It may still further comprise at least one of a group comprising e) a powder and/or colorant, f) surfactant, g) crosslinked organopolysiloxane, h) silicone resin, and i) silicone lattice resin solution.

Although an excellent cosmetic material according to this invention can be obtained only from a) polyhydric alcohol-modified silicone, b) an oil base, c) a compound having an alcoholic hydroxyl group in its molecular structure, and d) water, e) a powder and/or colorant, f) surfactant, g) crosslinked organopolysiloxane, h) silicone resin and i) silicone mesh resin solution may be added if necessary.

In the cosmetic material of this invention, in addition to the silicone compound, the oil base b) can be used according to the purpose.

It is preferable that part or all of the oil base b) is a liquid at ordinary temperature, more preferable that part or all of the oil base comprises a silicone oil comprising a volatile silicone and/or a repeating unit of —[O—Si—]n- in the molecular skeleton, and most preferable that part or all of the oil base comprises a fluorine group or an amino group.

The oil base may be a solid, a semi-solid or a liquid if it is an oil base usually used for cosmetic materials.

Examples of natural animal and vegetable oils and fats and semi-synthetic oils and fats are avocado oil, linseed oil, almondoil, Chinese wax, eno oil, olive oil, cacaobutter, kapok wax, Japanese nutmeg oil, carnuba wax, liver oil, candelilla wax, beef tallow, cow foot marrow, beef bone marrow, hardening beef tallow, persic oil, whale wax, hardened oil, wheat germ oil, sesame oil, rice germ oil, rice polishing oil, saccharum officinarum wax, sasanqua oil, safflower oil, shea butter, Chinese tung oil, cinnamon oil, jojoba wax, shellac wax, turtle oil, soybean oil, tea seed oil, tsubaki oil, evening primrose oil, corn oil, lard, rape seed oil, Japanese tung oil, rice bran wax, embryo oil, germ oil, horse fat, par chic oil, palm oil, palm kernel oil, castor oil, hardened castor oil, castor oil fatty acid methyl ester, sunflower oil, grape oil, bayberry wax, jojoba oil, macadamia nut oil, beeswax, mink oil, cotton seed oil, cotton wax, haze wax, haze seed oil, montan wax, coconut oil, hardened coconut oil, tri-coconut oil fatty acid glyceride, mutton tallow, arachis oil, lanolin, liquefied lanolin, reduced lanolin, lanolin alcohol, hard lanolin, acetic acid lanolin, lanolin fatty acid isopropyl, hexyl laurate, POE lanolin alcohol ether, POE lanolin alcohol acetate, lanolin fatty acid polyethylene glycol, POE hydrogenation lanolin alcohol ether and egg yolk oil.

Examples of hydrocarbon oils are ozokerite, squalane, squalene, ceresin, paraffin, paraffine wax, liquid paraffin, pristane, polyisobutylene, microcrystalline wax and Vaseline; examples of higher fatty acids are lauric acid, myristic acid, palmitic acid, stearic acid, behenic acid, undecylenic acid, oleic acid, linolic acid, linolenic acid, arachidonic acid, eicosapentaenoic acid (EPA), docosa-hexaenoic acid (DHA) isostearic acid and 12-hydroxystearic acid.

Examples of higher alcohols are lauryl alcohol, myristyl alcohol, palmityl alcohol, stearyl alcohol, behenyl alcohol, hexadecyl alcohol, oleyl alcohol, isostearyl alcohol, hexyl dodecanol, octyl dodecanol, cetostearyl alcohol, 2-decyltetradecynol, cholesterol, phytosterol, POE cholesterol ether, monostearallyl glycerol ether (batyl alcohol) and monooleyl glyceryl ether (celachyl alcohol).

Examples of ester oils are diisobutyl adipate, 2-hexyl decyl adipate, di-2-heptyl undecyl adipate, N-alkylglycol monoisostearate, ceryl isostearate, trimethylolpropane triisostearate, ethylene glycol di-2-ethylhexanoate, cetyl 2-ethyl hexanoate, trimethylolpropane tri-2-ethylhexanoate, pentaerythritol-tetra-2-ethylhexanoate, cetyl octanoate., octyl dodecyl gum ester, olein oleate, octyldodecyl oleate, decyl oleate, neopentylglycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, N-lauryl-L-glutamic acid-2-octyldodecyl ester and diisosterallyl malate; examples of glyceride oils are acetoglyceryl, glyceryl trioctanoate, glyceryl triisostearate, glyceryl triisopalmitate, glyceryl monostearate, glyceryl di-2-heptylundecanoate, glyceryl trimyristate and myristic acid isostearic acid diglyceryl ester.

Examples of silicone oils are low viscosity to high viscosity organopolysiloxanes such as dimethylpolysiloxane, methylphenyl polysiloxane, methyl hydrogen polysiloxane and dimethyl siloxane methyl phenyl siloxane copolymer; cyclic siloxanes such as octamethylcyclotetrasiloxane, decamethyl-cyclopentasiloxane, dodecylmethylcyclohexasiloxane, etra-methyltetrahydrogen-cyclotetrasiloxane and tetramethyl-tetraphenyl-cyclotetra-siloxane; silicone rubber such as high polymer gum dimethylpolysiloxane and gum dimethylsiloxane-methylphenyl siloxane copolymer, and cyclosiloxane solutions of silicone rubber, trimethylsiloxysilicic acid, cyclosiloxane solutions of trimethylsiloxysilicic acid, higher alkoxy-modified silicones such as stearoxysilicone, higher fatty acid-modified silicone, alkyl-modified silicone, amino-modified silicone and fluorine-modified silicone.

Examples of fluorine type oil bases are perfluoropolyether, perfluoro decalin and perfluorooctane.

The compound c) which has one or more types of alcoholic hydroxyl group in the molecular structure may be used for the cosmetic material of this invention according to the purpose.

It is preferable that the compound c) which has an alcoholic hydroxyl group in the molecular structure is water-soluble and that it is a monohydric and/or a polyhydric alcohol, and more preferable that it is a water-soluble polymer.

The alcohols which can be added in this invention are lower alcohols such as ethanol and isopropanol, sugar alcohols such as sorbitol and maltose, and sterols such as cholesterol, sitosterol, phytosterol and lanosterol.

The water-soluble polymer may be a vegetable polymer such as gum arabic, gum tragacanth, galactan, carob gum, guar gum, karaya gum, carrageenan, pectin, agar, quince seed (marmelo), starch (rice, corn, potato, wheat), algae colloid, tranto gum and locust bean gum, microorganism polymers such as xanthan gum, dextran, saccinoglucan and pullulan, animal polymers such as collagen, casein, albumin and gelatin, starch polymers such as carboxymethyl starch and methylhydroxypropyl starch, cellulose polymers such as methyl cellulose, ethyl cellulose, methylhydroxypropyl cellulose, carboxymethyl cellulose, hydroxymethyl cellulose, hydroxypropyl cellulose, cellulose nitrate, cellulose sodium sulfate, sodium carboxymethyl cellulose, crystalline cellulose, and cellulose powder, alginic acid polymers such as sodium alginate and alginic acid propyleneglycol ester, vinyl polymers such as polyvinylmethylether and carboxyvinyl polymer, polyoxyethylene polymers, polyoxyethylene polyoxypropylene copolymer polymers, acrylic polymers such as sodium polyacrylate, polyethyl acrylate and polyacrylamide, other synthetic water-soluble polymers such as polyethyleneimine and cation polymers, and inorganic water-soluble polymers such as bentonite, magnesium aluminium silicate, montmorillonite, beidellite, nontronite, saponite, hectorite and silicic acid anhydride.

Moreover, film-forming agents such as polyvinyl alcohol and polyvinyl pyrrolidone are also included in these water-soluble polymers.

The cosmetic material of this invention further comprises water d) as a component. The content of the water d) in the cosmetic material of this invention is 0–90.0 weight %, the blending proportion varying according to the type of cosmetic material.

The powder and/or colorant e) can be further used in the cosmetic material of this invention according to the purpose.

It is desirable that some or all of the powder and/or colorant e) are at least one or more of a silicone resin, a powder having a silicone elastomer as skeleton, and an organic powder having a repeating structural unit of —[O—Si—]n- in the skeleton.

If used for ordinary cosmetic materials, the powder can take any form (spheres, needles and plates), have any particle diameter (haze, powders, pigments) and any particle structure (porous, non-porous). Examples are inorganic powders, organic powders, surfactant metal salt powders, colored pigments, pearl pigments, metal powder pigment and natural colorants.

Examples of inorganic powders are titanium oxide, zirconium oxide, zinc oxide, cerium oxide, magnesium oxide, barium sulfate, calcium sulfate, magnesium sulfate, calciumcarbonate, magnesium carbonate, talc, mica, kaolin, sericite, muscovite, synthetic mica, phlogopite, red mica, biotite, lithia mica, silicic acid, silicic acid anhydride, aluminium silicate, magnesium silicate, magnesium aluminium silicate, calcium silicate, barium silicate, strontium silicate, tungstic acid metal salts, hydroxyapatite, vermiculite, haidingerite, bentonite, montmorillonite, hectorite, zeolite, ceramic powder, calcium diphosphate, alumina, aluminium hydroxide, boron nitride and silica.

Example of organic powders are polyamide powder, polyester powder, polyethylene powder, polypropylene powder, polystyrene powder, polyurethane, benzoguanamine powder, polymethyl-benzoguanamine powder, tetrafluoroethylene powder, polymethylmethacrylate powder, cellulose, silk powder, nylon powder, 12 nylon, 6 nylon, silicone powder, styrene-acrylic acid copolymer, divinylbenzene-styrene copolymer, vinyl resin, urea resin, phenol resin, fluororesin, silicone resin, acrylic resin, melamine resin, epoxy resin, polycarbonate resin, microcrystalline fiber powders, starch powder and lauroyl lysine.

Examples of surfactant metal salt powders (metallic soaps) are zinc stearate, aluminum stearate, calcium stearate, magnesium stearate, zinc myristate, magnesium myristate, zinc cetyl phosphorate, calcium cetyl phosphate and zinc sodium cetyl phosphate.

Examples of colored pigments are inorganic red pigments such as ferric oxide, iron hydroxide and ferric titanate, inorganic brown pigments such as gamma-iron oxide, inorganic yellow pigments such as yellow iron oxide and ochre, inorganic black pigments such as black iron oxide and carbon black, inorganic purple pigments such as manganese violet and cobalt violet, inorganic green pigments such as chromium hydroxide, chromium oxide, cobalt oxide and cobalt titanate, inorganic blue pigments such as cobalt and titanic acid cobalt, Prussian blue and ultramarine blue, tar colorant lake, natural colorant lake, and synthetic resin powders comprising combinations of these powders.

Example of pearl pigments are titanium oxide-coated mica, titanium oxide-coated mica, bismuth oxychloride, titanium oxide-coated bismuth oxychloride, titanium oxide-coated talc, scales foil and titanium oxide-coated colored mica; examples of metal powder pigments are aluminium powder, copper powder and stainless steel powder.

Examples of tar colorants are Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203', Orange No. 204, Orange No. 206 and Orange No. 207; examples of natural colorants are powders chosen from carminic acid, laccaic acid, carthamine, brazilin and crocin.

To the extent that it does not interfere with the purpose of this invention, one, two or more complexes of these powders, or materials processed with common oil bases, silicone oils, fluorine compounds and surfactants other than those of this invention, may also be used if necessary.

One, two or more of the surfactants f) can also be used for the cosmetic material of this invention.

It is preferable that the surfactant f) is a modified silicone which has a polyoxyalkylene chain in the molecule, and more preferable that HLB is 2–8.

The surfactant may be anionic, cationic, non-ionic or amphoteric, there being no limitation thereupon provided it is used in ordinary cosmetic materials. Specific examples of anionic surfactants are fatty acid soaps such as sodium stearate and triethanolamine palmitate, alkyl ether carboxylic acids and their salts, condensate salts of aminoacids and fatty acids, alkane sulfonates, alkene sulfonates, sulfonates of fatty acid esters, sulfonates of fatty acid amides, formalin condensation sulfonates, sulfate ester salts such as alkylsulfate ester salts, secondary higher alcohol sulfate ester salts, alkyl and allyl ether sulfate ester salts, sulfate ester salts of fatty acid esters, sulfate ester salts of fatty acid alkyloylamides and Turkey red oil, alkylphosphates, ether phosphates, alkyl allyl ether phosphates, amide phosphates and N-acyl aminoacid activators; cationic surfactants such as amines, i.e., alkylamine salts, polyamines and aminoalcohol fatty acid derivatives, alkyl quartenary ammonium salts, aromatic quartenary ammonium salts, pyridium salts and imidazolium salt; nonionic surfactants such as sorbitan fatty acid esters, glycerol fatty acid esters, polyglycerol fatty acid esters, propylene glycol fatty acid esters, polyethylene glycol fatty acid esters, cane sugar fatty acid esters, polyoxyethylene alkyl ethers, polyoxypropylene alkyl ethers, polyoxyethylene alkylphenyl ethers, polyoxyethylene fatty acid esters, polyoxyethylene sorbitan fatty acid esters, polyoxyethylene sorbitol fatty acid esters, polyoxyethylene glycerol fatty acid esters, polyoxyethylene propylene glycol fatty acid esters, polyoxyethylene castor oil, polyoxyethylene hardened castor oil, polyoxyethylene phytostanol ether, polyoxyethylene phytosterol ether, polyoxyethylene cholestanol ether, polyoxyethylene cholesteril ether, polyoxyalkylene-modified organopolysiloxanes, polyoxy-alkylenealkyl co-modified organopolysiloxanes, alkanol-amides, sugar ether and sugar amides; and examples of amphoteric surfactants are betaine, aminocarboxylates and imidazoline derivatives.

One, two or more of the crosslinked organopolysiloxanes g) can also be used for the cosmetic material of this invention.

It is preferable that the crosslinked organopolysiloxane contains and swells relative to 0.65–10.0 mm$^2$/s low viscosity silicone including low viscosity silicone equal to or more than its own weight.

It is also preferable that the crosslinking agent in this crosslinked organopolysiloxane has two or more vinyl reactive sites in the molecule, and forms a crosslinked structure by reaction between hydrogen atoms directly bonded with silicon atoms. Further, it is preferred that this crosslinked organopolysiloxane comprises at least one kind of group chosen from polyoxyalkylene, alkyl, alkenyl, aryl and fluoroalkyl in the crosslinked molecule. The blending amount when the crosslinked organopolysiloxane is used is preferably 0.1–30 weight % and more preferably 1–10 weight % relative to the total amount of cosmetic material.

One, two or more acrylic/silicone grafts, or block copolymer silicone resins h) can also be used for the cosmetic material of this invention.

The silicone resin is preferably is an acrylic silicone resin which contains at least one kind chosen from a group comprising pyrolidone, long chain alkyl, polyoxyalkylene and fluoroalkyl in the molecule.

Further, a solution i) of one, two or more silicone lattice resins can also be used for the cosmetic material of this invention according to the purpose. The silicone lattice resin is generally known as MQ resin, and MT or MDT resin, is marketed in the form of a solution such as octamethylcyclotetrasiloxane, and may contain at least one kind chosen from a group comprising pyrolidone, long chain alkyl, polyoxyalkylene, fluoroalkyl and amino.

The blending amount when a silicone resin such as an acrylic/silicone graft or block copolymer, or silicone lattice resin is used, is preferably 0.1–20 weight % and more preferably 1–10 weight %, relative to the total amount of a cosmetic material.

To the extent that they do not impair the effect of this invention, the components usually used in cosmetic materials may also be used in the cosmetic material of this invention, such as oil-soluble gelatinizers, organic-modified clay minerals, resins, ultraviolet absorbers, moisturizers, preservatives, antiseptics, antibacterials, perfumes, salts, antioxidants, pH regulators, chelating agents, refrigerants, anti-inflammatory agents, skin beautifying agents (whiteners, cell activators, dry and rough skin improvement agents, blood circulation promoters, skin astringents and anti-sebarrhoica agents), vitamins, aminoacids, nucleic acids, hormones and clathrates.

Examples of oil-soluble gelatinizers are metal soaps such as aluminium stearate, magnesium stearate and zinc myristate, aminoacid derivatives such as N-lauroyl-L-glutamic acid and alpha, gamma-di-n-butylamine, dextrin fatty acid esters such as dextrin palmitic acid ester, dextrin stearic acid ester and dextrin 2-ethyl hexanoic acid palmitic acid ester, cane sugar fatty acid esters such as cane sugar palmitic acid ester and cane sugar stearic acid ester, benzylidene derivatives of sorbitol such as monobenzylidene sorbitol and dibenzylidene sorbitol, and organic-modified clay minerals such as dimethylbenzyldodecylammonium montmorillonite clay and dimethyl dioctadecylammonium montmorillonite clay.

Examples of ultraviolet absorbers, benzoic acid ultraviolet absorbers such as p aminobenzoic acid, anthranilic acid ultraviolet absorbers such as methyl anthranilate, salicylic acid ultraviolet absorbers such as methyl salicylate, cinnamic acid ultraviolet absorbers such as octyl paramethoxycinnamate, benzophenone ultraviolet absorbers such as 2,4-dihydroxybenzophenone, urocanic acid ultraviolet absorbers such as ethyl urocanate, and dibenzoylmethane ultraviolet absorbers such as 4-t-butyl-4'-methoxy-dibenzoylmethane.

Examples of moisturizers are glycerol, sorbitol, propylene glycol, dipropylene glycol, 1,3-butylene glycol, glucose, xylitol, maltitol, polyethylene glycol, hyaluronic acid, chondroitin sulfate, pyrolidone carboxylate, polyoxyethylene methyl glucoside and polyoxypropylene methyl glucoside.

Examples of antiseptics and preservatives are paraoxybenzoic acid alkyl ester, benzoic acid, sodium benzoate, sorbic acid, potassium sorbate and phenoxyethanol; examples of antibacterials are benzoic acid, salicylic acid, carbolic acid, sorbic acid, paraoxy-benzoic acid alkyl ester, parachloro meta-cresol, hexachlorophene, benzalkonium chloride, chlorohexidine chloride, trichloro-carbanilide, photosensitizers and phenoxyethanol.

Examples of antioxidants are tocopherol, butylated hydroxyanisole, dibutylhydroxytoluene and phytic acid; examples of pH regulators are lactic acid, citric acid, glycolic acid, succinic acid, tartaric acid, dl-malic acid, potassium carbonate, sodium bicarbonate and ammonium bicarbonate; examples of chelating agents are alanine, ethylene diamine tetraacetic acid sodium salt, sodium polyphosphate, sodium metaphosphate and phosphoric acid; examples of refrigerants are L-menthol and camphor; examples of anti-inflammatory agents are allantoin, glycylrrhzin and its salts, glycyrrhetinic acid and glycyrrhetinic acid stearyl ester, tranexamic acid and azulene.

Skin beautifier components are whiteners such as placenta extract, arbutin, glutathione and creeping saxifrage extract; cell activators such as royal jelly, photosensitizers, cholesterol derivatives, and calf's blood extract; dry, rough skin improvement agents; blood circulation promoters such as nonyl acid warenylamide, nicotinic acid benzyl ester, nicotinic acid beta-butoxyethyl ester, capsaicin, zingerone, cantharis tincture, ichthammol, caffeine, tannic acid, alphaborneol, nicotinic acid tocopherol, inositol hexanicotinate, cyclandelate, cinnarizine, tolazoline, acetylcholine, verapamil, cepharanthin and gamma-orizanol, skin astringents such as zinc oxide and tannic acid, and anti-sebarrhoica agents such as sulfur and thianthol.

Examples of vitamins are vitamin A such as vitamin A oil, retinol, retinal acetate and retinal palmitate; vitamin B, i.e, vitamin B2 such as riboflavin, riboflavin butyrate, flavin adenine nucleotide; vitamin B6 such as pyridoxine hydrochloride, pyridoxine dioctanoate and pyridoxine tripalmitate; vitamin B12 and its derivatives, and vitamin B15 and its derivatives; vitamin C such as L-ascorbic acid, L-ascorbic acid dipalmitic acid ester, L-ascorbic acid-2-sodium sulfate and dipotassium L-ascorbic acid phosphoric acid diester; vitamin D such as ergocalciferol and cholecalciferol; vitamin E such as alpha-tocopherol, beta-tocopherol, gamma-tocopherol, acetic acid dl-alpha-tocopherol, nicotinic acid dl-alpha-tocopherol and succinic acid dl-alpha-tocopherol; vitamin H, vitamin P, nicotinic acids such as nicotinic acid, benzyl nicotinate and nicotinamide, pantothenic acids such as calcium pantothenate, D-pantothenyl alcohol, pantothenyl ethyl ether and acetyl pantothenyl ethyl ether, and biotin.

Examples of amino acids are glycine, valine, leucine, isoleucine, serine, threonine, phenylalanine, arginine, lysine, aspartic acid, glutamic acid, cystine, cysteine, methionine and tryptophan; examples of nucleic acids are deoxyribonucleic acid; and examples of hormones are estradiol and ethenyl estradiol.

In this invention, the cosmetic material may be a skin care product such as a cosmetic lotion, milky lotion, cream, cleansing cream, massage product, cleansing agent, antiperspirant or a deodorant; a makeup product such as a foundation, makeup foundation, rouge, eye shadow, mascara, eyeliner or lipstick; or a hair product such as a shampoo, rinse or treatment. Various forms may be chosen for the product such as a liquid, emulsion, solid, paste, gel or spray.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLES

The invention will now be described referring to specific examples, but the invention is not limited to these.

In the following empirical formula, the $Me_3SiO$ group (or $Me_3Si$ group) is referred to as "M", the $Me_2SiO$ group is referred to as "D" and the HMeSiO group is referred to as "H". Units wherein the methyl group in M and D are modified by a substituent group are referred to as $M^R$ and $D^R$.

Siloxane Compound 1

282 g of a methylhydrogen polysiloxane represented by the average empirical formula $M_2H_2$ was introduced into a reactor, and a mixture of 174 g of pentamethylvinyldisiloxane and 0.1 g of a toluene solution containing 0.5 weight % chloroplatinic acid was dripped in and stirred at room temperature to obtained a branch polysiloxane.

210 g of diglycerol monoallyl ether, 210 g of isopropyl alcohol (IPA) and 0.1 g of an IPA solution of 0.5 weight % of chloroplatinic acid were introduced into another reactor, and the branch polysiloxane previously synthesized was dripped in under reflux of solvent.

The reaction product was heated under reduced pressure and the solvent was distilled off to obtain an organopolysiloxane represented by the average empirical formula $M_2 D^{R*1} D^{R*2}$.

In the formula, $R^{*1}$ and $R^{*2}$ represent the following.

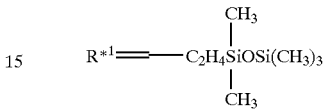

$R^{*2}=C_3H_6OCH_2CH(OH)CH_2OCH_2CH(OH)CH_2OH$

This product was a light yellow transparent liquid, viscosity 420 $mm^2$/s (25 degrees C.), specific gravity 0.982 (25 degrees C.) and refractive index 1.4363 (25 degrees C.).

Siloxane Compound 2

120 g of a methylhydrogencyclopolysiloxane represented by the average empirical formula $H_4$ was introduced into a reactor, and a mixture of 180 g of pentamethylvinyldisiloxane and 0.1 g of a toluene solution containing 0.5 weight % chloroplatinic acid was dripped in and stirred at room temperature to obtained a branch polysiloxane.

140 g of glycerol monoallyl ether, 140 g of isopropyl alcohol (IPA) and 0.1 g of an IPA solution of 0.5 weight % of chloroplatinic acid were introduced into another reactor, and the branch polysiloxane previously synthesized was dripped in under reflux of solvent.

The reaction product was heated under reduced pressure and the solvent was distilled off to obtain an organopolysiloxane represented by the average empirical formula $D^{R*1}_2 D^{R*3}_2$.

In the formula, $R^{*1}$ is the same as above, and $R^{*3}$ represents the following.

This product was a colorless, transparent liquid, viscosity 1650 $mm^2$/s (25 degrees C.), specific gravity 1.027 (25 degrees C.) and refractive index 1.4494 (25 degrees C.).

Siloxane Compound 3

320 g of a methylhydrogenpolysiloxane represented by the average empirical formula $M_2H_8$ was introduced into a reactor, and a mixture of 260 g of pentamethylvinyldisiloxane and 0.1 g of a toluene solution containing 0.5 weight % chloroplatinic acid was dripped in and stirred at room temperature to obtained a branch polysiloxane.

750 g of triglycerol monoallyl ether, 750 g of isopropyl alcohol (IPA) and 0.3 g of an IPA solution of 0.5 weight % of chloroplatinic acid were introduced into another reactor, and the branch polysiloxane previously synthesized was dripped in under reflux of solvent.

The reaction product was heated under reduced pressure and the solvent was distilled off to obtain an organopolysiloxane represented by the average empirical formula $M_2 D^{R*1}_3 D^{R*4}_5$.

In the formula, $R^{*1}$ is the same as above, and $R^{*4}$ represents the following.

This product was a colorless, transparent liquid, viscosity 174000 mPa.s (25 degrees C.) and refractive index 1.4687 (25 degrees C.).

Siloxane Compound 4

214 g of the methylhydrogenpolysiloxane represented by the average empirical formula $M_2H_8$ was introduced into a reactor, and a mixture of 714 g of an organopolysiloxane represented by the following average empirical formula (5) and 0.2 g of a toluene solution containing 0.5 weight % chloroplatinic acid was dripped in and stirred at room temperature to obtained a branch polysiloxane.

$$CH_2\!\!=\!\!CH(CH_3)_z\!\!-\!\!(SiO)_7\!\!-\!\!Si(CH_3)_zBu \quad (5)$$
(with CH$_3$ substituents on the central Si)

500 g of triglycerol monoallyl ether, 500 g of isopropyl alcohol (IPA) and 0.3 g of an IPA solution of 0.5 weight % of chloroplatinic acid were introduced into another reactor, and the branch polysiloxane previously synthesized was dripped in under reflux of solvent. The reaction product was heated under reduced pressure and the solvent was distilled off to obtain an organopolysiloxane represented by the average empirical formula $M_2D^{R*5}{}_3D^{R*4}{}_5$.

In the formula, $R^{*4}$ is the same as above, and $R^{*5}$ represents the following.

$$R^{\pm 5}\!\!=\!\!-\!\!C_2H_4-(SiO)_7-Si(CH_3)_2Bu$$
(with CH$_3$ substituents)

This product was a colorless, transparent liquid, viscosity 133600 mPa.s (25 degrees C.) and refractive index 1.4453 (25 degrees).

Silicone Compound 5

120 g of a methylhydrogenpolysiloxane represented by the average empirical formula $M_2D_{42}H_5$ was introduced into a reactor, and a mixture of 59 g of an organopolysiloxane represented by the following average empirical formula (6) and 0.2 g of a toluene solution $$CH_2\!\!=\!\!CH(CH_3)_2\!\!-\!\!(SiO)_{11}-Si(CH_3)_zBu \quad (6)$$
(with CH$_3$ substituents)

containing 0.5 weight % chloroplatinic acid was dripped in and stirred at room temperature to obtained a branch polysiloxane.

25 g of triglycerol monoallyl ether, 200 g of isopropyl alcohol (IPA) and 0.3 g of an IPA solution of 0.5 weight % of chloroplatinic acid were introduced into another reactor, and the branch polysiloxane previously synthesized was dripped in under reflux of solvent. The reaction product was heated under reduced pressure and the solvent was distilled off to obtain an organopolysiloxane represented by the average empirical formula $M_2D_{42}D^{R*6}{}_2D^{R*4}{}_3$.

In the formula, $R^{*4}$ is the same as above, and $R^{*6}$ represents the following.

$$R^{*6}\!\!=\!\!-\!\!C_2H_4-(SiO)_{11}-Si(CH_3)_zBu$$
(with CH$_3$ substituents)

This product was a colorless, transparent liquid, viscosity 1100 mm$^2$/s (25 degrees C.), specific gravity 0.990 (25 degrees C.) and refractive index 1.4150 (25 degrees C.).

Silicone Compound 6

110 g of an organopolysiloxane represented by the average empirical formula $M_2D_{40}H_8$ was introduced into a reactor, and a mixture of 60 g of an organopolysiloxane represented by the above average empirical formula (6) and 0.2 parts of a toluene solution containing 0.5 weight % of chloroplatinic acid was dripped in and reacted at 80 degrees C. for 3 hours.

Next, 48 g of oleylpolyoxypropylene (3) allyl ether (RG-125 made by Japan Emulsion (K.K.) was added, and the reaction completed by heating under reflux for 3 hours. 30 g of triglycerol monoallyl ether was then added, and reacted at 80 degrees C. for 3 hours.

The solvent was heated under reduced pressure and distilled off to obtain an organopolysiloxane represented by the average empirical formula $M_2D_{40}D^{R*6}{}_2D^{R*4}{}_3D^{R*7}{}_3$.

In the formula, $R^{*4}$ and $R^{*6}$ are the same as the above, and $R^{*7}$ represents the following.

$$R^{*7}\!\!=\!\!-\!\!C_3H_6O(C_3H_6O)_3C_{18}H_{35}$$

This product was a light brown, transparent liquid, viscosity 2000 mm$^2$/s (25 degrees C.), specific gravity 0.994 (25 degrees C.).

Siloxane Compound 7

32 g of a methylhydrogenpolysiloxane represented by the average empirical formula $M_2H_8$ was introduced into a reactor, and a mixture of 17.5 g pentamethylvinyldisiloxane and 0.1 g of a toluene solution containing 0.5 weight % of chloroplatinic acid was dripped in and stirred at room temperature to obtain a branch polysiloxane.

150 g of a 60% IPA solution of an allyl glyceride (a mixture of alpha- and beta-types containing approximately 10 wt % of dimer), 150 g of isopropyl alcohol (IPA) and 0.1 g of an IPA solution containing 0.5 weight % of chloroplatinic acid were introduced into another reactor, and the branch polysiloxane previously obtained was dripped in under reflux of solvent. The solvent was heated under reduced pressure and distilled off to obtain an organopolysiloxane represented by the average empirical formula $M_2D^{R*1}{}_2D^{R*8}{}_6$.

In the formula, $R^{*1}$ is the same as the above, and $R^{*8}$ is represented by the following formula.

$R^{*8}$:—$C_3H_6O$—[pyranose ring with substituents CH$_2$OH, OH, OH, OH]

Siloxane Compound 8

300 g of a methylhydrogenpolysiloxane represented by the average empirical formula $M_2D_{10}H_5$ was introduced into a reactor, and a mixture of 440 g of the organopolysiloxane represented by the following average empirical formula (6) and 0.1 g of a toluene solution containing 0.5 weight % of chloroplatinic acid was dripped in and stirred at room temperature to obtain a branch polysiloxane. 370 g of a 60% IPA solution of an allyl glycoside, 370 g of isopropyl alcohol (IPA) and 0.1 g of an IPA solution containing 0.5 weight % of chloroplatinic acid were introduced into another reactor, and the branch polysiloxane previously obtained was dripped in under reflux of solvent. The solvent was heated under reduced pressure and distilled off to obtain an organopolysiloxane represented by the average empirical formula $M_2D^{R^{*6}}{}_2D^{R^{*8}}{}_3$. In the formula, $R^{*6}$ and $R^{*8}$ are the same as the above.

Examples 1–7 and Comparative Examples 1–4

Cleanser Compositions

Cleanser compositions were prepared by blending the compositions shown in Table 1, and evaluated by the following method regarding appearance, and user feeling and usability in lipstick.

The compositions and results are shown in Table 1.

Evaluation Method:

1. Appearance

-transparent; -translucent; x-Opaque

2. User Feeling and Usability

User tests were performed, and an evaluation made according to the following criteria regarding ease of spreading, compatibility with dirt, removal of dirt and clean skin feel after use. The evaluation was made in terms of average points.

Evaluation Criteria:

| | |
|---|---|
| 5 points: | Very good |
| 4 points: | Good |
| 3 points: | Normal |
| 2 points: | Rather poor |
| 1 point: | Poor |

Evaluation:

| | |
|---|---|
| .: | average mark 4.5 or higher |
| .: | average mark 3.5 to less than 4.5 |
| .: | average mark 2.5 to less than 3.5 |
| X: | average mark less than 2.5 |

The following compounds were used in the following examples.

Polyoxyethylene (10) sorbitan monolaurate: Sanyo Chemical Industries, Ltd.
Polyoxyethylene (6) sorbitan monolaurate: Sanyo Chemical Industries, Ltd.
Polyoxyethylene (10) monooleate: Japan Emulsion, Ltd., EMALEX OE-10
Polyoxyethylene (8) oleyl ether: Japan Emulsion, Ltd. EMALEX 510
Polyoxyethylene (15) isocetyl ether: Sanyo Chemical Industries, Ltd.
Polyoxyethylene (6) lauryl ether: Toho Chemical Industry Co., Ltd. Pegnol L-6
Polyoxyethylene (50) hardened castor oil: Nikko Chemicals, Inc., HCO-50
Glycerol: Nippon Oils & Fats Co., Ltd.
Glycerol monolaurate: Sanyo Chemical Industries, Ltd.
Lauryl dimethylamine oxide: Nippon Oil & Fats Co., Ltd., Unisafe A-LM
Propylene glycol: Nisso Oil Industries, Ltd.
Dipropylene glycol: Nisso Oil Industries, Ltd.

TABLE 1

| | Examples | | | | | | |
|---|---|---|---|---|---|---|---|
| | 1 | 2 | 3 | 4 | 5 | 6 | 7 |
| POE(10) sorbitan monolaurate: | 30 | 30 | 30 | — | — | — | — |
| Purified water | 50 | 50 | 50 | 50 | 50 | 50 | 50 |
| Siloxane compound 1 | 20 | — | — | — | — | — | — |
| Siloxane compound 2 | — | 20 | — | 20 | 20 | 20 | 20 |
| Siloxane compound 7 | — | — | 20 | — | — | — | — |
| POE(8) oleyl ether | — | — | — | 30 | — | — | — |
| POE(50) hardened castor oil | — | — | — | — | 30 | — | — |
| POE(10) monooleate | — | — | — | — | — | 30 | — |
| Glycerol monolaurate | — | — | — | — | — | — | 30 |
| Appearance | — | — | — | — | — | — | — |
| Spreadability | — | — | — | — | — | — | — |
| Compatibility with dirt | — | — | — | — | — | — | — |
| Removal of dirt | — | — | — | — | — | — | — |
| Clean skin feel after use | — | — | — | — | — | — | — |

| | Comparative Examples | | | |
|---|---|---|---|---|
| | 1 | 2 | 3 | 4 |
| POE(10) sorbitan monooleate: | 30 | 30 | 30 | 30 |
| Purified water | 70 | 50 | 50 | 50 |
| Polyether-modified silicone 1 | — | 20 | — | — |
| Polyether-modified silicone 2 | — | — | 20 | — |
| Polyether-modified silicone 3 | — | — | — | 20 |
| Appearance | — | — | — | — |
| Spreadability | X | — | — | — |
| Compatibility with dirt | X | — | — | — |
| Removal of dirt | — | — | — | — |
| Clean skin feel after use | X | — | — | — |

Polyether-modified silicone 1: KF6011, Shin-Etsu Chemical Industries Ltd., molecular weight 4500, HLB = 14
Polyether-modified silicone 2: KF6013, Shin-Etsu Chemical Industries Ltd., molecular weight 4000, HLB = 10
Polyether-modified silicone 3: KF6017, Shin-Etsu Chemical Industries Ltd., molecular weight 6000, HLB = 4.5

As can be seen from the results of Table 1, compared to the Comparative Examples 1–4, the cleanser compositions of Examples 1–7 of this invention have a transparent appearance, rapid compatibility with lipstick and are very easy to remove. They also spread easily, leave a clean skin feel and are very pleasant to use.

Example 8

Makeup Remover

A makeup remover comprising the following components was prepared.

| (Component) | (%) |
|---|---|
| 1. POE(10) sorbitan monolaurate | 10.0 |
| 2. Siloxane compound 1 | 20.0 |

| (Component) | (%) |
|---|---|
| 3. Sorbitol | 10.0 |
| 4. Carrageenan | 0.5 |
| 5. Glycerol | 5.0 |
| 6. Preservatives | Suitable amount |
| 7. Perfume | Suitable amount |
| 8. Purified water | remainder |

Manufacturing Method

A: Components 1–6 and 8 were added, and dissolved uniformly.

B: Component 7 was added to A to obtain the makeup remover.

When foundation was removed using the makeup remover obtained as described above, it was found to have good compatibility with the foundation and good removing power, and spread easily. The remover also left a clean skin feeling, was very easy to use and was very pleasant to use.

Example 9

Hair Cosmetic Product Remover

A hair cosmetic product remover comprising the following components was prepared.

| (Component) | (%) |
|---|---|
| 1. Polyoxyethylene (15) isocetyl Ether | 10.0 |
| 2. Siloxane compound 2 | 20.0 |
| 3. 1,3-butylene glycol | 10.0 |
| 4. Glycerol | 10.0 |
| 5. Carrageenan | 0.5 |
| 6. Preservatives | Suitable amount |
| 7. Perfume | Suitable amount |
| 8. Purified water | remainder |

Manufacturing Method

A: Components 1–6 and 8 were added, and dissolved uniformly.

B: Component 7 was added to A to obtain the hair cosmetic product remover.

When the hair was washed using the cosmetic product remover obtained as described above, it was found to have good compatibility with the hair and sebum together with good removing power, and spread easily. The remover also left no sticky feeling, was very easy to use and was very pleasant to use.

Example 10

Face Cleanser

A face cleanser comprising the following components was prepared.

| (Component) | (%) |
|---|---|
| 1. Polyoxyethylene (6) lauryl ether | 5.0 |
| 2. Siloxane compound 7 | 10.0 |

| (Component) | (%) |
|---|---|
| 3. Ethanol | 10.0 |
| 4. Lauryl dimethylamine oxide | 2.0 |
| 5. Propylene glycol | 3.0 |
| 6. Preservatives | Suitable amount |
| 7. Perfume | Suitable amount |
| 8. Purified water | remainder |

Manufacturing Method

A: Components 1–6 and 8 were added, and dissolved uniformly.

B: Component 7 was added to A to obtain the face cleanser.

When the face cleanser obtained as above was used, it was found to have good compatibility with cosmetics and sebum together with good removing power, and spread easily. The cleanser also left no sticky feeling, left a clean skin feel, was easy to use and very pleasant to use.

Example 11

Makeup Remover

A makeup remover comprising the following components was prepared.

| (Component) | (%) |
|---|---|
| 1. Polyoxyethylene (6) sorbitan monolaurate | 5.0 |
| 2. Siloxane compound 1 | 5.0 |
| 3. Siloxane compound 2 | 15.0 |
| 4. Ethanol | 10.0 |
| 5. Glycerol | 2.0 |
| 6. Dipropylene glycol | 3.0 |
| 7. Preservatives | Suitable amount |
| 8. Perfume | Suitable amount |
| 9. Purified water | remainder |

Manufacturing Method

A: Components 1–7 and 9 were added, and dissolved uniformly.

B: Component 8 was added to A to obtain the makeup remover.

When the makeup remover obtained as above was used, it was found to have good compatibility with cosmetics and sebum together with good removing power, and spread easily. The makeup remover also left no sticky feeling, left a clean skin feel, was easy to use and very pleasant to use.

Example 12

Lipstick

A lipstick comprising the following components was prepared.

| (Component) | (%) |
|---|---|
| 1. Palmitic acid/dextrin ethylhexanoate | 9.0 |
| 2. Glyceryl trioctanoate | 22.0 |

-continued

| (Component) | (%) |
| --- | --- |
| 3. Bentonite | 10.0 |
| 4. Siloxane compound 4 | 1.5 |
| 5. Decamethylcyclopenasiloxane | 42.0 |
| 6. 1.3-butylene glycol | 5.0 |
| 7. Purified water | 19.8 |
| 8. Colorants | Suitable amount |

Manufacturing Method

A: Component 1, part of Component 2 and Components 3–5 were blended, and dissolved.

B: Component 8 was blended with the remainder of Component 2, and dispersed by a roller.

C: B) was added to A), and blended uniformly.

D: Components 6, 7 were blended, and the mixture heated.

E: D) was added to C), and the mixture emulsified.

The lipstick obtained as above was a W/o cream lipstick having excellent cosmetic lasting power. It was found to spread easily, was not sticky and was not oily.

Example 13

Eye Liner

An eye liner comprising the following components was prepared.

| | (Component) | (%) |
| --- | --- | --- |
| 1. | Octamethylcyclotetrasiloxane | remainder |
| 2. | Siloxane compound 5 | 3.0 |
| 3. | Silicone lattice resin | 15.0 |
| 4. | Dioctadecyl dimethylammonium salt-modified montmorillonite | 3.0 |
| 5. | Silicone-treated black iron oxide | 10.0 |
| 6. | 1,3-butylene glycol | 5.0 |
| 7. | Preservatives | Suitable amount |
| 8. | Perfume | Suitable amount |
| 9. | Purified water | 10.0 |

Silicone lattice resin: 50% D5 solution of silicone lattice compound having $[Me_3SiO_{1/2}]/[SiO_2]$ ratio of 0.8

Silicone-treated black iron oxide: 2% methylhydrogenpolysiloxane was added to black iron oxide, and the mixture was heated.

Manufacturing Method

A: Components 1–4 were blended, Component 5 was added, and the mixture dispersed uniformly by blending.

B: Components 6–8 and 10 were blended.

C: After B was added to A and emulsified, Component 9 was added to obtain the eye liner.

It was found that the eye liner obtained above spread easily and was easy to apply, and had a cool, clean feel. It did not change with temperature or time, was very easy to use and very safe. Moreover, it had excellent water-resistance and anti-perspirant properties, and it lasted well as a cosmetic.

Example 14

Eye Shadow

An eye shadow comprising the following components was prepared.

| | (Component) | (%) |
| --- | --- | --- |
| 1. | Decamethylcyclopentasiloxane | 15.0 |
| 2. | Dimethylpolysiloxane (6 mm$^2$/s) | 10.0 |
| 3. | Siloxane compound 4 | 2.0 |
| 4. | PEG (10) lauryl ether | 0.5 |
| 5. | Silicone-treated chromium oxide (N.B.1) | 6.2 |
| 6. | Silicone-treated ultramarine blue (N.B.1) | 4.0 |
| 7. | Silicone-treated titanium-coated mica (N.B.1) | 6.0 |
| 8. | Sodium chloride | 2.0 |
| 9. | Propylene glycol | 8.0 |
| 10. | Preservatives | Suitable amount |
| 11. | Perfume | Suitable amount |
| 12. | Purified water | remainder |

(N.B.1) Silicone treatment: after addition of 3% of methylhydrogen polysiloxane to the powder, it was heated Manufacturing Method A: Components 1–4 were blended, Components 5–7 were added the mixture dispersed uniformly.

B: Components 8–10 and 12 were dissolved uniformly.

C: B was added to A with stirring to obtain an emulsion, and Component 11 was added to obtain the eye shadow.

It was found that the eye shadow obtained above spread easily, was not oily or powdery, and had a fresh, clean feel. It had excellent water-resistance, water repellence and good anti-perspirant properties, and did not easily disintegrate. It did not change with temperature or time, and was very stable.

Example 15

Sun Tan Lotion

A sun tan lotion comprising the following components was prepared.

| | (Component) | (%) |
| --- | --- | --- |
| 1. | Emulsifier composition | 6.0 |
| 2. | Dimethylpolysiloxane (20 mm$^2$/s) | 49.0 |
| 3. | 1,3-butylene glycol | 5.0 |
| 4. | Dehydrosodium acetate | Suitable amount |
| 5. | Antioxidant | Suitable amount |
| 6. | Preservatives | Suitable amount |
| 7. | Perfume | Suitable amount |
| 8. | Purified water | remainder |
| (N.B.1) Emulsifier composition | | |
| a. | Siloxane composition 4 | 10.0 weight parts |
| b. | Dioctadecyldimethylammonium salt-modified montmorillonite | 10.0 weight parts |
| c. | Ethanol | 40.0 weight parts |

Manufacturing Method

A: Component a was dissolved in c, and Component b was added.

B: A was stirred for 1 hour, and ethanol was evaporated off in an evaporator.

C: B was dried for one day and night at 50 degrees C. to obtain an emulsifier composition of Component 1.

D: Components 1 and 2 obtained in C were blended.

E: Components 3–6 and 8 were blended uniformly.

F: E was added to D with stirring, and Component 7 was added to obtain a sun tan lotion.

It was found that the sun tan lotion obtained above had a fine consistency, spread easily, was not oily or powdery and had a fresh, clean feel. It had excellent water-resistance, water repellence and good anti-perspirant properties, and did not easily disintegrate. It did not change with temperature or time, and was very stable.

Example 16

Sun Cut Cream

A sun cut cream comprising the following components was prepared.

| | (Component) | (%) |
|---|---|---|
| 1. | Decamethylcyclopentasiloxane | 17.5 |
| 2. | KP545 | 12.0 |
| 3. | Glyceryl triisoocatanoate | 5.0 |
| 4. | Octyl paramethoxycinnamate | 6.0 |
| 5. | KSG21 | 5.0 |
| 6. | Siloxane compound 6 | 1.0 |
| 7. | Lipophilic-treated zinc oxide | 20.0 |
| 8. | Sodium chloride | 0.5 |
| 9. | 1,3-butylene glycol | 2.0 |
| 10. | Preservatives | Suitable amount |
| 11. | Perfume | Suitable amount |
| 12. | Purified water | remainder |

KP545: acryl silicone resin/decamethylcyclopentasiloxane solution (Shin-Etsu Chemical Industries, Ltd.).

KSG21: crosslinked silicone resin/dimethylpolysiloxane (6 mm$^2$/s) solution (Shin-Etsu Chemical Industries, Ltd.).

Manufacturing Method

A: Component 2 was dissolved in part of Component 1, rendered homogeneous, and Component 7 was added and dispersed in a bead mill.

B: The remainder of Component 1 and 3–6 were blended, and mixed uniformly.

C: Components 8–10 and 12 were blended, and dissolved.

D: C was added to B and emulsified, then A and Component 11 was added to obtain the sun cut cream.

It was found that the sun cut cream thus obtained was not sticky, and spread easily with good skin contact. It was highly compatible with the skin, produced a lustrous finish and lasted very well. It was also very stable to temperature and time.

Example 17

Sun Tan Cream

A sun tan cream comprising the following components was prepared.

| | (Component) | (%) |
|---|---|---|
| 1. | Decamethylcyclopentasiloxane | 15.0 |
| 2. | Dimethylpolysiloxane (100 mm$^2$/s) | 5.0 |
| 3. | KP561 | 0.5 |
| 4. | Siloxane compound 8 | 6.0 |
| 5. | Palmitic acid | 0.2 |
| 6. | Dimethyloctylparaminobenzoic acid | 0.5 |
| 7. | 4-t-butyl-4'-methoxy-dibenzoylmethane | 0.5 |
| 8. | Kaolin | 0.5 |
| 9. | Red iron oxide | 0.2 |
| 10. | Yellow iron oxide | 0.3 |
| 11. | Black iron oxide | 0.1 |
| 12. | Titanium oxide-coated mica | |
| 13. | Sodium L-glutamate | 3.0 |
| 14. | 1,3-butylene glycol | 5.0 |
| 15. | Dioctadecyldimethylammonium chloride | 0.1 |
| 16. | Antioxidants | Suitable amount |
| 17. | Preservatives | Suitable amount |
| 18. | Perfume | Suitable amount |
| 19. | Purified water | remainder |

Manufacturing Method

KP561: stearallyl-modified acryl silicone (Shin-Etsu Chemical Industries, Ltd.).

A: Components 1–7 and 16–17 are heated and dissolved.

B: After heating and stirring part of Components 15 and 19, Components 8–12 were added and dispersed.

C: Components 13–14 and the remainder of Component 19 were dissolved uniformly, and blended with B.

D: C was gradually added to A with stirring to emulsify it, the mixture was cooled, and Component 18 was added to obtain the sun tan cream.

It was found that the sun tan cream obtained above had a fine consistency, spread easily, was not sticky or oily, and had a moist, fresh, clean feel. It had excellent compatibility with the skin, lasted well, showed no change such as separation or powder agglomeration with temperature or time, and was very stable.

Example 18

Foundation

A foundation comprising the following components was prepared.

| | (Component) | (%) |
|---|---|---|
| 1. | Decamethylcyclopentasiloxane | 45.0 |
| 2. | Dimethylpolysiloxane (6 mm$^2$/s) | 5.0 |
| 3. | Siloxane compound 4 | 1.5 |
| 4. | Siloxane compound 6 | 0.5 |
| 5. | Octyldecyldimethylbenzylammonium salt-modified mont-morillonite | 4.0 |
| 6. | Hydrophobic-treated titanium oxide *1 | 10.0 |
| 7. | Hydrophobic-treated talc *1 | 6.0 |
| 8. | Hydrophobic-treated mica *1 | 6.0 |
| 9. | Hydrophobic-treated red iron oxide *1 | 1.6 |
| 10. | Hydrophobic-treated yellow iron oxide *1 | 0.7 |
| 11. | Hydrophobic-treated black iron oxide *1 | 0.2 |
| 12. | Dipropylene glycol | 5.0 |
| 13. | Paraoxybenzoic acid methyl ester | 0.3 |
| 14. | 2-amino-methyl-1,3-propandiol | 0.2 |
| 15. | Hydrochloric acid | 0.1 |

-continued

| (Component) | (%) |
| --- | --- |
| 16. Perfume | Suitable amount |
| 17. Water | remainder |

*1 Hydrophobic treatment: after addition of 2% of methyl-hydrogen polysiloxane to the powder, it was heated Manufacturing Method A: Components 1–5 were heated and blended, Components 6–11 were added, and the mixture was homogenized.

B: Components 12–15 and 17 were heated and dissolved (pH of the aqueous system was 9.0).

C: B was gradually added to A with stirring to obtain an emulsion, the mixture was cooled, and Component 16 was added to obtain the foundation.

It was found that the foundation obtained above had a fine consistency, spread easily without being sticky or oily, was moist and fresh, and had a clean feel. It also lasted well, did not change with temperature or time, and was very stable.

Example 19

Liquid Foundation

A liquid foundation comprising the following components was prepared.

| (Component) | (%) |
| --- | --- |
| 1. Decamethylcyclopentasiloxane | 16.0 |
| 2. Dimethylpolysiloxane (6 mm²/s) | 8.0 |
| 3. Octyl paramethoxycinnamate | 3.0 |
| 4. 12-hydroxystearic acid | 1.0 |
| 5. Siloxane compound 5 | 15.0 |
| 6. Fluorine-modified silicone (N.B.1) | 5.0 |
| 7. Spherical silicons resin powder (N.B.2) | 3.0 |
| 8. Fluorine compound-treated particulate titanium oxide (N.B.3) | 8.0 |
| 9. Fluorine compound-treated titanium mica (N.B.3) | 1.0 |
| 10. Fluorine compound-treated titanium oxide (N.B.3) | 5.0 |
| 11. Fluorine compound-treated red iron oxide (N.B.3) | 0.9 |
| 12. Fluorine compound-treated yellow iron oxide (N.B.3) | 2.0 |
| 13. Fluorine compound-treated black iron oxide (N.B.3) | 1.0 |
| 14. Ethanol | 15.0 |
| 15. Glycerol | 3.0 |
| 16. Magnesium sulfate | 1.0 |
| 17. Preservatives | Suitable ammount |
| 18. Perfume | Suitable ammount |
| 19. Purified water | remainder |

(N.B.1) Fluorine-modified silicone: FL-100 (Shin-Etsu Chemical Industries Ltd.)
(N.B.2) Spherical silicone resin powder: KMP590 (Shin-Etsu Chemical Industries Ltd.)
(N.B.3) Fluorine-compound treated: 5% coated by diethanolamine salt of perfluoroalkylethylphosphoric acid Manufacturing Method A: Components 7–13 are blended uniformly.

B: Components 1–6 were heated to 70 degrees C. and blended together, then A was added, and dispersed uniformly.

C: Components 14–17 and 19 were heated to 40 degrees C., added gradually to B to form an emulsion, cooled, and Component 18 was added to form a liquid foundation.

It was found that the liquid foundation obtained above was not sticky, spread easily, and had a very clean, cool feel. It also did not change with temperature or time, and was very stable.

Example 20

Hair Cream

A hair cream comprising the following components was prepared.

| (Component) | (%) |
| --- | --- |
| 1. Decamethylcyclopentasiloxane | 10.0 |
| 2. Methylphenylpolysiloxane | 5.0 |
| 3. Squalene | 4.0 |
| 4. Silicone lattice resin | 1.0 |
| 5. Glyceryl dioleic acid | 2.0 |
| 6. Siloxane compound 4 | 4.0 |
| 7. Sodium sorbitol sulfuric acid | 2.0 |
| 8. Sodium chondroitin sulfate | 0.5 |
| 9. Sodium hyaluronate | 0.5 |
| 10. Propylene glycol | 3.0 |
| 11. Preservatives | 1.5 |
| 12. Vitamin E acetate | 0.1 |
| 13. Antioxidants | Suitable amount |
| 14. Perfume | Suitable amount |
| 15. Purified water | remainder |

Silicone lattice resin: 50% D5 solution of silicone lattice compound having [Me$_3$SiO$_{1/2}$]/[SiO$_2$] ratio of 0.8

Manufacturing Method

A: Components 1–6 and 11–12 were heated and blended.

B: Components 7–10 and 15 were heated and dissolved.

C: B was gradually added to A with stirring to obtain an emulsion, cooled, and Component 14 was added to obtain a hair cream.

It was found that the hair cream obtained above spread easily, was not sticky or oily, and had a moist, fresh, clean feel. It had excellent water-resistance, water repellence and good anti-perspirant properties, and lasted well. It did not change with temperature or time, and was very stable.

Example 21

Hair Cream

A hair cream comprising the following components was prepared.

| (Component) | (%) |
| --- | --- |
| 1. Silicone gum solution (40000 mPa · s) | 18 |
| 2. Silicone lattice resin | 6 |
| 3. Glyceryl tri-2-ethylhexanoate | 8 |
| 4. Vaseline | 5 |
| 5. Stearallyl alcohol | 2 |
| 6. Sorbitan monooleic acid | 2 |
| 7. Siloxane compound 6 | 2 |
| 8. Glycerol | 5 |
| 9. Perfume | Suitable amount |
| 10. Purified water | remainder |

Silicone lattice resin: 50% D5 solution of silicone lattice compound having [Me$_3$SiO$_{1/2}$]/[SiO$_2$] ratio of 0.8

Manufacturing Method

The above hair cream was prepared according to the following procedure.

A: Components 1–7 were heated to 70 degrees C.

B: Components 8–10 were mixed and stirred, and Component (A) was added to obtain an emulsion.

It was found that the hair cream obtained above gave the hair luster and softness, and gave an excellent perm to the hair.

Example 22

Moisturizing Cream

A moisturizing cream comprising the following components was prepared.

| (Component) | (%) |
|---|---|
| 1. Decamethylcyclopentasiloxane | 10.0 |
| 2. Methylphenylpolysiloxane | 3.0 |
| 3. Liquid paraffin | 5.0 |
| 4. KF-7002 | 8.0 |
| 5. Siloxane compound 8 | 2.0 |
| 6. Organopolysiloxane elastomer spherical powder | 2.5 |
| 7. Hydrophobic-treated silica | 2.0 |
| 8. Zinc stearate | 2.0 |
| 9. Vitamin E acetate | 3.0 |
| 10. Polyethylene glycol 400 | 1.0 |
| 11. Sodium lactate | 1.0 |
| 12. 1,3-butylene glycol | 5.0 |
| 13. Preservatives | Suitable amount |
| 14. Perfume | Suitable amount |
| 15. Purified water | remainder |

KF-7002: Stearallyl-modified silicone (Shin-Etsu Chemical Industries Ltd.)
Organopolysiloxane elastomer spherical powder: KMP594 (Shin-Etsu Chemical Industries Ltd.)
Hydrophobic-treated silica: Aerosil R972 (Japan Aerosil)

Manufacturing Method

A: Components 1–5 and 8–9 were blended uniformly, Components 6–7 were added, and the mixture dispersed uniformly.

B: Components 10–13 and 15 were added and dissolved.

C: B was gradually added to A to obtain an emulsion, cooled, and Component 14 was added to obtain a moisturizing cream.

It was found that the moisturizing cream obtained above spread easily, had a fresh and clean feel, and was not sticky. It did not change with temperature or time, and was very stable in use.

Example 23

Hand Cream

A hand cream comprising the following components was prepared.

| (Component) | (%) |
|---|---|
| 1. Decamethylcyclopentasiloxane | 30.0 |
| 2. Liquid paraffin | 10.0 |
| 3. Amino-modified silicone gum (amino equivalents 70000 g/mol) | 15.0 |
| 4. Siloxane compound 4 | 4.0 |
| 5. Distearallyldimethylammonium chloride | 0.8 |
| 6. Vitamin E acetate | 0.1 |
| 7. Polyethylene glycol 4000 | 1.0 |
| 8. Glycerol | 10.0 |
| 9. Aluminum magnesium silicate | 1.2 |
| 10. Preservatives | Suitable amount |
| 11. Perfume | Suitable amount |
| 12. Purified water | remainder |

Manufacturing Method

A: Components 1–3 were heated, mixed and dissolved, and Components 2, 4–6 and 10 were heated and added, B: Components 7–9 and 12 were heated and blended.

C: B was added gradually to A to obtain an emulsion, cooled, and Component 11 was added to obtain a hand cream.

It was found that the hand cream obtained above was not sticky, spread easily and had a clean feel. It effectively protected the skin during washing up, and was very stable to temperature.

Example 24

O/W Hand Cream

An O/W hand cream comprising the following components was prepared.

| (Component) | (%) |
|---|---|
| 1. KP545 | 10.0 |
| 2. KP561 | 8.0 |
| 3. Cetanol | 1.0 |
| 4. Glyceryl triisostearate | 5.0 |
| 5. Stearic acid | 3.0 |
| 6. Glyceryl monostearate | 1.5 |
| 7. Siloxane compound 6 | 0.7 |
| 8. Sorbitan sesquioleic acid | 0.5 |
| 9. Polyoxyethylenesorbitan monooleic acid | 1.0 |
| 10. Sodium hydroxide (1% aqueous solution) | 10.0 |
| 11. 1,3-butylene glycol | 5.0 |
| 12. Preservatives | Suitable amount |
| 13. Perfume | Suitable amount |
| 14. Purified water | remainder |

KP545: acryl silicone resin/decamethylcyclopentasiloxane solution (Shin-Etsu Chemical Industries Ltd.)
KP561: stearallyl-modified acryl silicone resin (Shin-Etsu Chemical Industries Ltd.)

A: Components 1–9 were blended, heated and dissolved.

B: Components 10–12 and 14 were blended, and heated.

C: B was added to A to obtain an emulsion, cooled, and Component 13 was added to obtain an O/W hand cream.

It was found that the hand cream obtained above was not sticky, spread easily, had an intimate feel with good skin contact and a lustrous finish. It lasted very well, and was very stable to temperature and time.

Example 25

Emulsion

An emulsion comprising the following components was prepared.

| (Component) | (%) |
| --- | --- |
| 1. Decamethylcyclopentasiloxane | 15.0 |
| 2. Methylphenylpolysiloxane | 5.0 |
| 3. Squalene | 5.0 |
| 4. Pentaerythritol tetra-2-ethylhexanoate | 5.0 |
| 5. Siloxane compound 8 | 3.0 |
| 6. Organopolysiloxane elastomer spherical powder | 2.0 |
| 7. Hydrophobic-treated silica | 0.5 |
| 8. Magnesium ascorbate-phosphate | 1.0 |
| 9. Sodium chloride | 1.0 |
| 10. Polyethylene glycol 11000 | 1.0 |
| 11. Propylene glycol | 8.0 |
| 12. Preservatives | Suitable amount |
| 13. Perfume | Suitable amount |
| 14. Purified water | remainder |

Organopolysiloxane elastomer spherical powder: KMP594 (Shin-Etsu Chemical Industries Ltd.)
Hydrophobic-treated silica: Aerosil R972 (Japan Aerosil Ltd.)

Manufacturing Method

A: Components 1–5 were blended uniformly, Components 6–7 were added, and the mixture dispersed uniformly.

B: Components 8–10 were added gradually to Component 14, dissolved, and Components 11, 12 were added after homogenizing.

C: B was added gradually to A to obtain an emulsion, cooled, and Component 13 was added to obtain an emulsion.

It was found that the emulsion obtained above spread easily, had a dry feel without stickiness, did not change with temperature or time, and was very stable in use.

Example 26

Beauty Lotion

A beauty lotion comprising the following components was prepared.

| (Component) | (%) |
| --- | --- |
| 1. Decamethylcyclopentasiloxane | 12.0 |
| 2. Glyceryl triisooctanoate | 10.0 |
| 3. Siloxane compound 6 | 2.0 |
| 4. Siloxane compound 5 | 0.2 |
| 5. Glycerol | 10.0 |
| 6. Magnesium salt of ascorbic acid-phosphoric acid | 3.0 |
| 7. Sodium chloride | 2.0 |
| 8. Preservatives | Suitable amount |
| 9. Perfume | Suitable amount |
| 10. Purified water | remainder |

Manufacturing Method

A: Components 1–4 were heated and blended.

B: Components 5–8 and Component 10 were heated, and dissolved uniformly.

C: B was added gradually to A with stirring, cooled, and Component 9 was added to obtain a beauty lotion.

It was found that the beauty lotion obtained above had a fine consistency, spread easily without being sticky, was moist and fresh, did not change with temperature or time, and was very stable.

Example 27

Antiperspirant

An antiperspirant comprising the following components was prepared.

| (Component) | (%) |
| --- | --- |
| 1. Octamethylcyclopentasiloxane | 30.0 |
| 2. Siloxane compound 4 | 1.0 |
| 3. Polyoxyethylenesorbitan monooleic acid (20 E.O.) | 0.5 |
| 4. Glycine salt of aluminum-zirconium quartenary hydrate | 20.0 |
| 5. Water | remainder |

Manufacturing Method

A: Components 1–2 were blended.

B: Component 4 was dissolved in 5, and Component 3 was added.

C: B was added gradually to A with stirring to obtain an emulsion, and thereby obtain an antiperspirant.

It was found that the antiperspirant obtained above spread easily without being sticky or oily, did not become too white, had a clean feel, did not change with temperature or time, and was very stable.

Example 28

Cleansing Cream

A cleansing cream comprising the following components was prepared.

| (Component) | (%) |
| --- | --- |
| 1. Dimethylpolysiloxane (6 mm$^2$/s) | 5.0 |
| 2. Methylphenylpolysiloxane | 5.0 |
| 3. Liquid paraffin | 8.0 |
| 4. Jojoba oil | 2.0 |
| 5. Siloxane compound 4 | 2.5 |
| 6. Siloxane compound 6 | 0.5 |
| 7. Dextrin fatty acid ester | 0.8 |
| 8. Aluminum monostearate | 0.2 |
| 9. Aluminum chloride | 1.0 |
| 10. Glycerin | 10.0 |
| 11. Preservatives | Suitable amount |
| 12. Perfume | Suitable amount |
| 13. Purified water | remainder |

Manufacturing Method

A: Components 1–8 were heated and blended.

B: Component 9–11 and 13 were heated and dissolved.

C: B was added gradually to A with stirring to obtain an emulsion, cooled, and Component 12 was added to obtain a cleansing cream.

It was found that the cleansing cream obtained above had a fine consistency, spread easily without being sticky or oily, was moist and fresh, and had a clean feel. It had a good cleansing effect, did not change with temperature or time, and was very stable.

Example 29

Treatment Gel

A treatment gel comprising the following components was prepared.

| (Component) | (%) |
|---|---|
| 1. Ethanol | 20.0 |
| 2. Siloxane compound 3 | 0.5 |
| 3. Glyceryl triisooctanoate | 3.0 |
| 4. KF-7002 | 2.0 |
| 5. KSP-100 | 8.0 |
| 6. Carboxyvinyl powder (1% aqueous solution) | 20.0 |
| 7. Triethanolamine | 0.2 |
| 8. Purified water | 46.3 |

KF-7002: Stearallyl-modified silicone (Shin-Etsu Chemical Industries Ltd.)

Manufacturing Method

A: Components 1–5 were blended and dispersed.

B: Component 6–8 were blended uniformly.

C: B was added gradually to A, and blended uniformly.

It was found that the treatment gel obtained above spread easily without being sticky or oily, was moist and fresh, and had a clean feel. It adapted easily to the skin, did not change with temperature or time, and was very stable.

Example 30

Wash-Off Cosmetic Pack

A wash-off cosmetic pack comprising the following components was prepared.

| (Component) | (%) |
|---|---|
| 1. Dimethylpolysiloxane (6 mm$^2$/s) | 3.0 |
| 2. Siloxane compound 7 | 2.0 |
| 3. Kaolin | 30.0 |
| 4. Carboxyvinyl polymer | 0.4 |
| 5. 1.3-butylene glycol | 10.0 |
| 6. Glycerol | 20.0 |
| 7. Preservatives | Suitable amount |
| 8. Perfume | Suitable amount |
| 9. Purified water | remainder |

Manufacturing Method

A: Components 1–2 and Component 8 were blended.

B: Components 4–7 and 9 were blended uniformly, Component 3 was blended and the mixture stirred.

C: B was added gradually to A to obtain an emulsion, and thereby obtain a paste type wash-off cosmetic pack.

It was found that the wash-off cosmetic pack obtained above spread easily when it was applied and a good cleansing effect. After washing off, the skin was left feeling moist, without stickiness, and smooth. It was very easy to use, and was very stable.

Example 31

Deodorant

A deodorant comprising the following components was prepared.

| (Component) | (%) |
|---|---|
| 1. Decamethylcyclopentasiloxane | 12.0 |
| 2. Dimethylpolysiloxane (6 mm$^2$/s) | 4.0 |
| 3. Siloxane compound 4 | 1.0 |
| 4. Propylene glycol | 31.0 |
| 5. Triclosan | 0.1 |
| 6. Glycerol | 15.0 |
| 7. Preservatives | Suitable amount |
| 8. Perfume | Suitable amount |
| 9. Purified water | remainder |

Manufacturing Method

A: Components 1–3 were blended.

B: Component 5 was dissolved in 4, and Components 6–9 were blended.

C: While stirring A vigorously, B was added to obtain an emulsion.

D: 65 parts of C and 35 parts of a spraying agent (n-butane, isobutene, propane mixture) were added to an aerosol can to obtain an aerosol.

It was found that the deodorant obtained above did not drip even when used at high concentration, was not sticky, was dry, had a lasting effect, and was very easy to use.

The cosmetic products containing the siloxane compound of this invention spread easily, were not sticky or oily, were moist and fresh, and had a clean feel. They lasted very well, did not change with temperature or time, and were very stable.

The invention also provides cosmetic products which when blended with skin cleansing compositions, in addition to the above feeling in use, ease of use and stability with time, were highly compatible with cosmetics and sebum, and were very effective in removing dirt.

The entire disclosure of all applications, patents and publications, cited herein and of corresponding JP application No. 2000-374342, filed Dec. 8, 2000, and U.S. patent application Ser. No. 10/005,672, filed Dec. 7, 2001 are incorporated by reference herein.

The proceeding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A polyhydric alcohol-modified silicone having the formula (1):

   (1)

wherein R$^1$ is, identical or different, a 1–30 carbon atom alkyl group, aryl group, aralkyl group, fluorine-substituted alkyl group, amino-substituted alkyl group or carboxyl-substituted alkyl group, or an organic group of the formula (2):

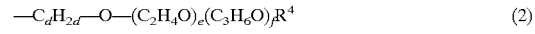   (2)

wherein R$^4$ is a hydrocarbon group having 4–30 carbon atoms, or R$^5$—(CO)— wherein R$^5$ is a hydrocarbon group having 1–30 carbon atoms, d, e and f are integers in the range, respectively, $0 \leq d \leq 15$, $0 \leq e \leq 5$, and $0 \leq f \leq 50$;

$R^2$ is of the formula (3):

-Q-O—X    (3)

wherein Q is a bivalent hydrocarbon group having 3–20 carbon atoms which may contain at least an ether linkage or ester bond, and X is a polyhydric alcohol-substituted hydrocarbon group which has at least two hydroxyl groups;

$R^3$ is an organosiloxane having the formula (4):

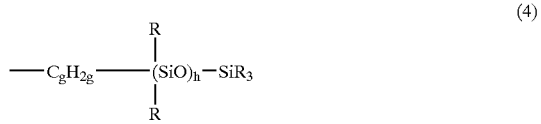

wherein R groups each represent a 1–30 carbon atom alkyl group, aryl group, aralkyl group or fluorinated alkyl group, g and h are integers in the range, respectively, $1 \leq g \leq 5$, and $0 \leq h \leq 500$, and a, b and c are in the range, respectively, $1.0 \leq a \leq 2.5$, $0.001 \leq b \leq 1.5$, and $0.001 \leq c \leq 1.5$.

2. A polyhydric alcohol-modified silicone as defined in claim 1, wherein X is a glycerin or a sugar derivative.

3. A polyhydric alcohol-modified silicone as defined in claim 1, wherein $R^2$ is of the formula:

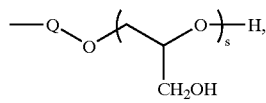

wherein each of s and t is an integer of 1–20.

4. A polyhydric alcohol-modified silicone as defined in claim 1, wherein X is a sugar residue derived from a monosaccharide, an oligosaccharide or a polysaccharide.

5. A polyhydric alcohol-modified silicone as defined in claim 1, wherein X is a sugar residue derived from glycosyl, mannosyl, galactosyl, ribosyl, arabinosyl, xylosyl, fructosyl, maltosyl, cellobiosyl, lactosyl, maltotriosyl, cellulose, or starch.

6. A polyhydric alcohol-modified silicone as defined in claim 1, wherein at least one $R^1$ is methyl, ethyl, propyl, butyl, pentyl, hexyl, heptyl, octyl, nonyl, decyl, cyclopentyl, cyclohexyl, phenyl, tolyl, benzyl, phenethyl, trifluoropropyl, heptadecafluorodecyl, 3-amino propyl, 3-[(2-amino ethyl) amino]propyl, or 3-carboxypropyl.

7. A polyhydric alcohol-modified silicone as defined in claim 1, wherein 50% or more of the $R^1$ groups are methyl.

8. A polyhydric alcohol-modified silicone as defined in claim 1, wherein 50% or more of the $R^1$ and/or R groups are methyl.

9. A polyhydric alcohol-modified silicone as defined in claim 1, wherein $R^1$ and/or R are methyl.

10. A polyhydric alcohol-modified silicone as defined in claim 1, wherein h is an integer of 1–50.

11. A polyhydric alcohol-modified silicone as defined in claim 1, wherein Q is —(CH$_2$)$_2$—, —(CH$_2$)$_3$—, —CH$_2$CH(CH$_3$)CH$_2$—(CH$_2$)$_4$—, —(CH$_2$)$_5$—, —(CH$_2$)$_6$—, —(CH$_2$)$_7$—, —(CH$_2$)$_8$—, —(CH$_2$)$_2$—CHCH$_2$CH$_2$CH$_3$)—, —CH$_2$—CH(CH$_2$CH$_3$)—, —(CH$_2$)$_3$—O—(CH$_2$)$_2$—, —(CH$_2$)$_3$—O—(CH$_2$)$_2$—O—(CH$_2$)$_2$—, —(CH$_2$)$_3$—O—CH$_2$CH(CH$_3$)—, or —CH$_2$—CH(CH$_3$)—COO(CH$_2$)$_2$—.

12. A cosmetic material comprising polyhydric alcohol-modified silicone as defined in claim 1.

13. A cosmetic material as defined in claim 12, further comprising at least one an oil base, a compound having an alcoholic hydroxyl group in the molecule, or water.

14. A cosmetic material as defined in claim 12, comprising at least one species of a powder and/or colorant, surfactant, crosslinked organopolysiloxane, silicone resin, or silicone lattice resin solution.

15. A skin care product comprising the cosmetic material as defined claim 12.

16. A product as defined in claim 15 in the form of a liquid, milky lotion, cream, solid, paste, gel, powder, multilayer composition, mousse, or spray.

17. A hair product comprising the cosmetic material as defined in claim 12.

18. An antiperspirant product comprising the cosmetic material as defined in claim 12.

19. A makeup product comprising the cosmetic material as defined in claim 12.

20. An ultraviolet radiation defense product comprising the cosmetic material as defined in claim 12.

* * * * *